United States Patent [19]
Dirks et al.

[11] Patent Number: 5,846,246
[45] Date of Patent: *Dec. 8, 1998

[54] DUAL-BALLOON RAPID-EXCHANGE STENT DELIVERY CATHETER WITH GUIDEWIRE CHANNEL

[75] Inventors: Richard Dirks, Assen; Wilhelmus Petrus Martinus Maria van Erp, Leek; Henderikus Smit, Schoonoord, all of Netherlands

[73] Assignee: Cordis Corporation, Miami Lakes, Fla.

[*] Notice: This patent issued on a continued prosecution application filed under 37 CFR 1.53(d), and is subject to the twenty year patent term provisions of 35 U.S.C. 154(a)(2).

[21] Appl. No.: 595,344

[22] Filed: Feb. 1, 1996

Related U.S. Application Data

[63] Continuation of Ser. No. 546,245, Oct. 20, 1995, abandoned.

[30] Foreign Application Priority Data

Oct. 21, 1994 [NL] Netherlands ............................ 9401758
Feb. 15, 1995 [NL] Netherlands ............................ 9500283

[51] Int. Cl.⁶ .................................................... A61F 11/00
[52] U.S. Cl. ........................... 606/108; 604/101; 604/102; 606/194
[58] Field of Search ................................. 604/101–2, 96; 128/660.01–660.02, 662.06, 656–8, 772, 692; 606/108, 194

[56] References Cited

U.S. PATENT DOCUMENTS

| | | |
|---|---|---|
| 4,148,307 | 4/1979 | Utsugi . |
| 4,430,083 | 2/1984 | Ganz et al. . |
| 4,563,180 | 1/1986 | Jervis et al. . |
| 4,665,925 | 5/1987 | Millar ................................. 128/662.06 |
| 4,762,129 | 8/1988 | Bonzel . |
| 4,771,777 | 9/1988 | Horzewski et al. ..................... 604/101 |
| 4,943,278 | 7/1990 | Euteneuer et al. ......................... 604/96 |
| 4,983,169 | 1/1991 | Furukawa . |
| 4,990,139 | 2/1991 | Jang . |
| 5,002,532 | 3/1991 | Gaiser et al. . |
| 5,040,548 | 8/1991 | Yock . |
| 5,046,503 | 9/1991 | Schneiderman .......................... 604/102 |
| 5,061,257 | 10/1991 | Martinez et al. . |
| 5,061,273 | 10/1991 | Yock . |
| 5,085,649 | 2/1992 | Flynn . |
| 5,180,367 | 1/1993 | Kontos et al. ........................... 604/101 |
| 5,226,889 | 7/1993 | Sheiban . |
| 5,232,445 | 8/1993 | Bonzel . |
| 5,267,594 | 12/1993 | Nita et al. . |
| 5,312,328 | 5/1994 | Nita . |
| 5,336,184 | 8/1994 | Teirstein . |
| 5,358,487 | 10/1994 | Miller . |
| 5,380,307 | 1/1995 | Chee et al. . |
| 5,496,275 | 3/1996 | Sirhan et al. ............................. 604/102 |
| 5,533,968 | 7/1996 | Muni et al. .............................. 604/102 |
| 5,569,184 | 10/1996 | Crocker et al. . |
| B1 4,762,129 | 8/1988 | Bonzel . |

FOREIGN PATENT DOCUMENTS

| | | |
|---|---|---|
| 0274846 | 7/1988 | European Pat. Off. . |
| 0345051 | 12/1989 | European Pat. Off. . |
| 0442657 | 8/1991 | European Pat. Off. . |
| 0260107 | 6/1992 | European Pat. Off. . |
| 0277370 | 6/1992 | European Pat. Off. . |
| 0528039 | 2/1993 | European Pat. Off. . |

(List continued on next page.)

*Primary Examiner*—Mark Bockelman
*Attorney, Agent, or Firm*—Michael Montgomery; Thomas Vigil

[57] ABSTRACT

The catheter comprises a tube-like basic body having a proximal end, a distal end section, a distal end and a central lumen; two active elements, at least one of which is a balloon, mounted on the distal end section of the basic body; the basic body further having a wall hole located at a position in between the distal end and the proximal end and close to a proximal end of the most proximal of the two active elements; a separate tube-like member received in the central lumen of the basic body and extending from an end hole at the distal end of the basic body to the wall hole and fixed close to the wall hole for receiving a guide wire.

4 Claims, 5 Drawing Sheets

FOREIGN PATENT DOCUMENTS

| | | | |
|---|---|---|---|
| 0595308 | 5/1994 | European Pat. Off. . | |
| 072860 | 5/1970 | German Dem. Rep. | 604/101 |
| 2659238 | 9/1977 | Germany . | |
| 3833359 | 4/1990 | Germany . | |
| 9401744 | 10/1994 | Netherlands . | |
| 9401758 | 10/1994 | Netherlands . | |
| 9401759 | 10/1994 | Netherlands . | |
| 9500284 | 2/1995 | Netherlands . | |
| WO9320882 | 10/1993 | WIPO . | |
| WO9321835 | 11/1993 | WIPO . | |
| WO9402196 | 2/1994 | WIPO . | |

DUAL-BALLOON RAPID-EXCHANGE STENT DELIVERY CATHETER WITH GUIDEWIRE CHANNEL

CROSS REFERENCE TO RELATED APPLICATIONS

This application is a continuation of U.S. application Ser. No. 08/546,245 filed Oct. 20, 1995, now abandoned.

BACKGROUND OF THE INVENTION

1. Field of the Invention

The present invention relates to a catheter which can be introduced into a patient by means of a guide wire. First, a guide wire is introduced into the patient and advanced to the position to which an active element of the catheter is to be advanced. Next, the distal end of the catheter, which is to be inserted, is passed over the proximal end of the guide wire and advanced further along this guide wire, whereby the active element is advanced to the desired position inside the body of the patient.

2. Description of the Related Art Including Information Disclosed Under 37 CFR §§ 1.97–1.99

Various catheters that mount at least two balloons, that are used in the implantation of a stent or that are introduced into a blood vessel with the assistance of a guidewire are disclosed in the following listed, analogous and non-analogous, U.S. Patents and foreign and PCT patent publications:

|  | Patentee |
| --- | --- |
| U.S. Pat. No. | |
| 4,148,307 | Utsugi |
| 4,762,129 | Bonzel |
| B1 4,762,129 | |
| 4,990,139 | Jang |
| 5,002,532 | Gaiser et al. |
| 5,040,548 | Yock |
| 5,061,273 | Yock |
| 5,226,889 | Sheiban |
| 5,232,445 | Bonzel |
| 5,358,487 | Miller |
| 5,336,184 | Teirstein |
| German Patent Publications: | |
| DE 26 59 238 | Utsugi |
| DE 38 33 359 | Bockenheimer, et al. |
| European Patent Publications: | |
| EP 0 260 107 | Jang |
| EP 0 274 846 | Rosenbluth |
| EP 0 277 370 | Gaiser et al. |
| EP 0 345 051 | Rosenbluth, et al. |
| EP 0 442 657 | Ryan et al. |
| EP 0 528 039 | Igaki et al. |
| EP 0 595 308 | Solar et al. |
| PCT Publications: | |
| WO 93/20882 | Motasim Sirhan et al. |
| WO 93/21835 | Nita et al. |
| WO 94/02196 | Lee |

SUMMARY OF THE INVENTION

According to the present invention there is provided a catheter comprising a tube-like basic body having a proximal end, a distal end section, a distal end and a central lumen; two active elements, at least one of which is a balloon, mounted on the distal end section of the basic body; the basic body further having a wall hole located at a position in between the distal end and the proximal end and close to a proximal end of the most proximal of the two active elements; a separate tube-like member received in the central lumen of the basic body and extending from an end hole at the distal end of the basic body to the wall hole and fixed close to the wall hole for receiving a guide wire.

On introduction, the catheter according to the present invention is subjected to relatively little friction on the guide wire, which simplifies the introduction.

Only the extreme distal end section of the catheter is guided and not the entire basic body.

The guide wire lumen extends as a smooth and continuous surface from the end hole to the wall hole, so that inserting the guide wire into the guide wire lumen does not cause any problems. The catheter according to this embodiment can furthermore be manufactured relatively easy from separate tube-like elements with a single lumen. Complicated multi-lumen profiles are consequently superfluous.

DESCRIPTION OF THE PREFERRED EMBODIMENT(S)

Figure 1:
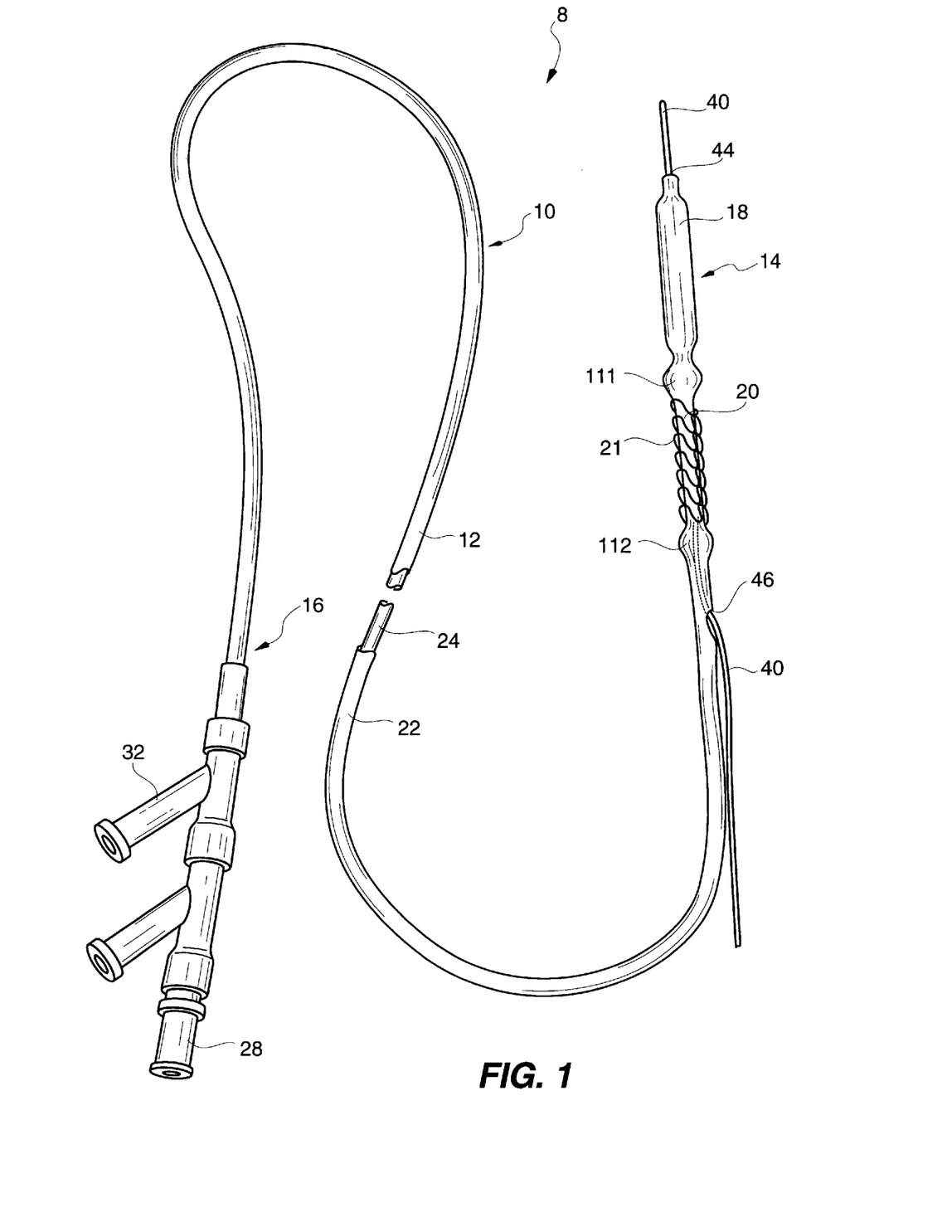
FIG. 1 is a perspective view, with portions broken away, of a catheter assembly constructed according to the teachings of the present invention.
Figure 2:
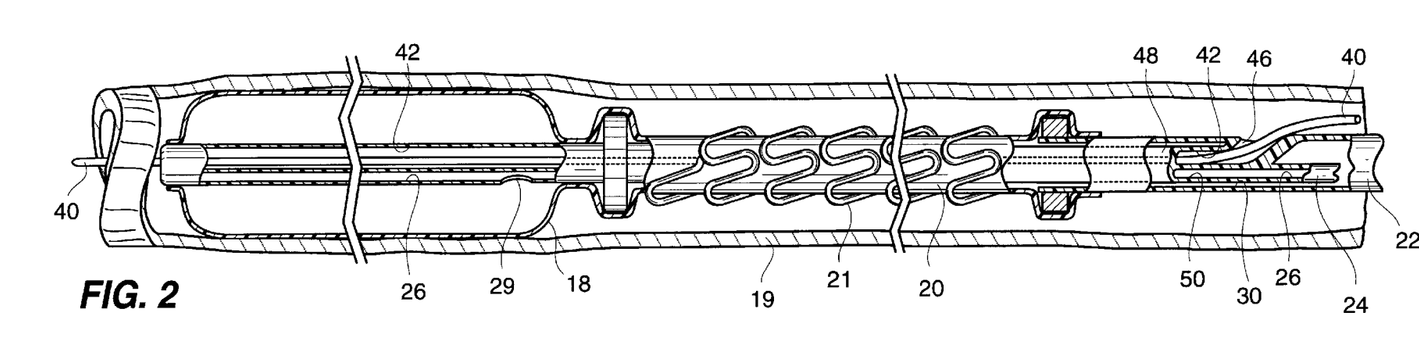
FIG. 2 is longitudinal view, with portions broken away, of a distal end section of a catheter of the catheter assembly shown in FIG. 1.

The catheter assembly 8 constructed according to the teachings of the present invention includes a catheter 10 which is shown in FIG. 1 and which comprises a tube-like basic tubular body 12 with a distal end 14 and a proximal end 16. At the distal end 14, two balloons 18 and 20 have been arranged. The distal balloon 18 is used for dilating a narrowed section 19 of a blood vessel (FIG. 2). The relatively proximal balloon 20 has a stent 21 arranged thereon when the proximal balloon 20 is in a compressed state. This stent 21 can be expanded by means of inflation of the proximal balloon 20 and thus be implanted in the section 19 of the vessel dilated beforehand by means of the distal balloon 18.

With the embodiment shown, the basic tubular body 12 comprises an outer tube-like element 22 and an inner tube-like element 24. A lumen 26 (FIG. 2) inside the inner tube-like element 24 can be connected at the proximal end 16 of the catheter 10 to a coupling 28, and, at a distal end opening 29, to the inside of the distal balloon 18 in order to convey medium under pressure from the coupling 28 to the distal balloon 18 in order to expand the latter.

In between the inner tube-like element 24 and the outer tube-like element 22, an annular lumen 30 is formed which, at the proximal end 16 of the catheter 10, is connected to a coupling 32 and at a distal end to the inside of the proximal balloon 20 in order to be able to expand the latter in a similar manner.

For introducing the catheter 10 into a patient, a guide wire 40 is employed in the usual manner. For the purpose of receiving this guide wire 40, a lumen 42 has been formed in the catheter 10 which extends from an end hole 44 (FIG. 1) to a wall hole 46 in the catheter 10. This wall hole 46 has been arranged in the wall of the basic tubular body 12 at a position in between the distal end 14 and the proximal end 16 of the catheter 10.

With the preferred embodiment shown in FIG. 1, the wall hole 46 has been arranged close to the relatively proximal active element, proximal balloon 20, of the catheter 10. The lumen 42 for receiving the guide wire 40 only extends therefore through the distal end section of the catheter 10.

As FIG. 2 illustrates in greater detail, the guide wire lumen 42 has been formed inside a double-lumen element 48. The other lumen 50 of this element 48 is connected with the lumen 26 of the inner tube-like element 24 of the basic tubular body 12. The medium under pressure supplied via the coupling 28 flows through the annular interspace 30 between the double-lumen element 48 and the outer tube-like element 22 and, via the hole 29 in the wall of this double-lumen element 48, into the balloon 18 for dilating a narrowed section 19 in a blood vessel.

Figure 3:
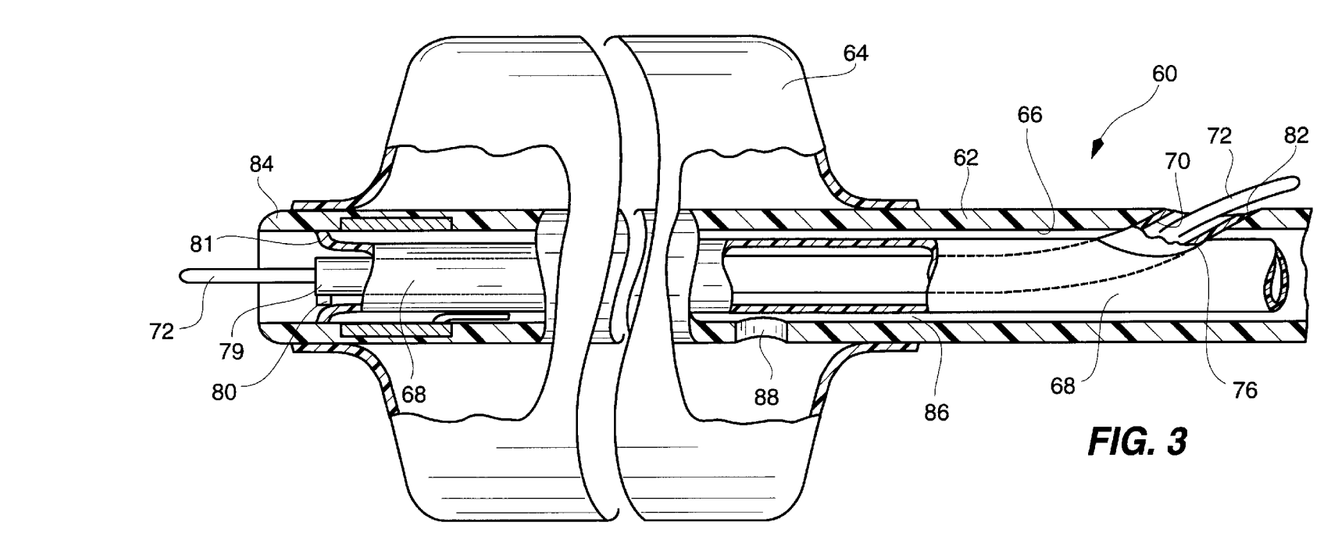
FIG. 3 is a longitudinal view, with portions broken away. of a distal end section of another embodiment of a catheter constructed according to the teachings of the present invention.

In FIG. 3 is illustrated another embodiment of a catheter 60 constructed according to the teachings of the present invention. An outer tube-like element 62 of the catheter 60 carries a balloon 64. In a central lumen 66 of this outer tube-like element 62, an inner tube-like element 68 has been received through which for instance a contrast medium can be supplied. With this catheter 60, a lumen 70 for a guide wire 72 has been formed by the lumen 70 of a separate tube-like element 76 which has an end 79, viewing the end-section on the left-hand side shown in FIG. 3, that has been fixed at 80 close to the distal end 81 of the inner tube-like element 68 and has been attached at the other end in an opening 82 in the outer tube-element 62. During the manufacturing process, the separate tube-like element 76 is pushed through the opening 82 until the end 79 is situated close to the distal end 84 of the outer tube-like element 62. Subsequently, the tube-like element 76 is fixed all round in the opening 82, for instance by gluing or ultrasonic welding. Next, the protruding section of the tube-like element 76 is beveled off and finished until it forms a smooth transition with the outer wall of the outer tube-like element 62.

With this embodiment, an annular interspace 86 is formed in between the outer tube-like element 62 and the inner tube-like element 68 for supplying medium under pressure to the balloon 64 via an opening 88 in the outer wall of the outer tube-like element 62 and for the discharge of medium from there.

Figure 4:
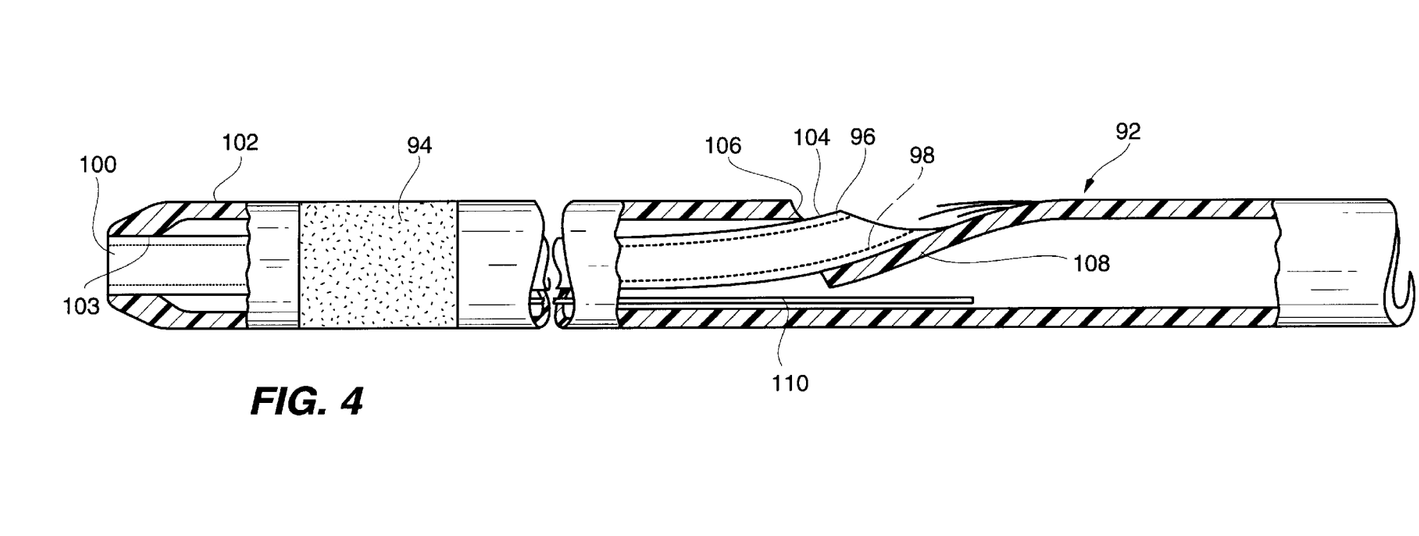
FIG. 4 is a longitudinal view, with portions broken away. of a distal end section of still another embodiment of a catheter constructed according to the teachings of the present invention.

FIG. 4 shows a distal end-section of a catheter 92 which has been provided with an ultrasonic sensor 94 as one active element.

Also in this case, a separate tube-like element 96 has been employed of which the lumen 98 forms the guide wire lumen of the catheter 92. At a distal end 100, the separate tube-like element 96 has been attached to an outer tube-like element 102 of the catheter 92 at 103 in such a manner as to form a seal, by, for instance, gluing or ultrasonic welding.

The other end 104 of the separate tube-like element 96 has been fixed close to a wall hole 106 inside the outer tube-like element 102. A relatively proximal wall section 108 of the basic tubular body formed by the tube-like element 102 has been folded inward, and the relatively proximal end of the separate tube-like element 96 has been fixed on this inwardly folded wall section 108. As can be seen clearly in FIG. 4, the proximal wall section 108 of the tube-like element which forms a basic tubular body 102 forms a very even transition from the lumen of the separate tube-like element 96 to the outside. The basic tubular body 102 is fixed all around to the proximal end-section of the separate tube-like element 96, thus creating a seal. Lines 110 connected to the ultrasonic sensor 94 extend through the central lumen of tube-like element 102 forming the basic tubular body 102 to the proximal end of the catheter 92, and are at that point connected to a processing device.

Figure 5:
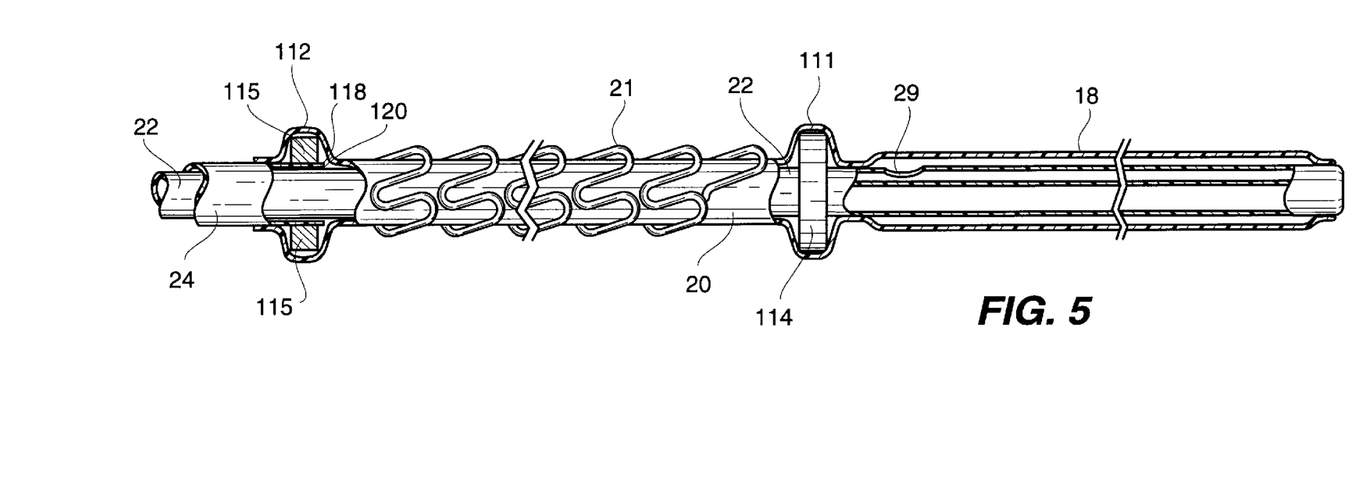
FIG. 5 is a longitudinal view, with portions broken away, of the distal end of the catheter shown in FIG. 1.

As shown in FIGS. 1 and 5, on both sides of the balloon member 20, the catheter 10 has been provided with bulges 111 and 112. The compressed stent 21 is arranged around the balloon 18 in between those bulges 111 and 112. The stent 21 is enclosed by the bulges 111 and 112 in the axial direction of the catheter 10, so that it cannot slide off the balloon 20.

As can be seen in FIG. 5 et seq. in particular, the bulges 111 and 112 in this embodiment are formed by respective rings 114 and 115 which have been received inside the balloon 20. The ring 114 has been arranged around the continuous inner tube-like element 24 and the ring 115 has been arranged around an end 118 of the outer tube-like element 22. As the rings 114, 115 have been arranged inside the balloon 20 they do not interfere with the unfolding of the balloon 20, and the balloon forms a smooth "skin" over the rings 114, 115, which is favorable when introducing the catheter 10.

The distal end 14 of the catheter 10 is introduced into a narrowed section 19 of a blood vessel of a patient inside of which the stent 21 is to be implanted. The embodiment of the catheter 10 shown here is provided with the balloon 18 for dilating a narrowed blood vessel section 19, in addition to the balloon 20 designed for expanding the stent 21. By employing the two balloons 18 and 20, dilating the vessel section 19 and implanting the stent 21 can be achieved using one and the same catheter 10, without it being necessary to change catheters.

Figure 6:
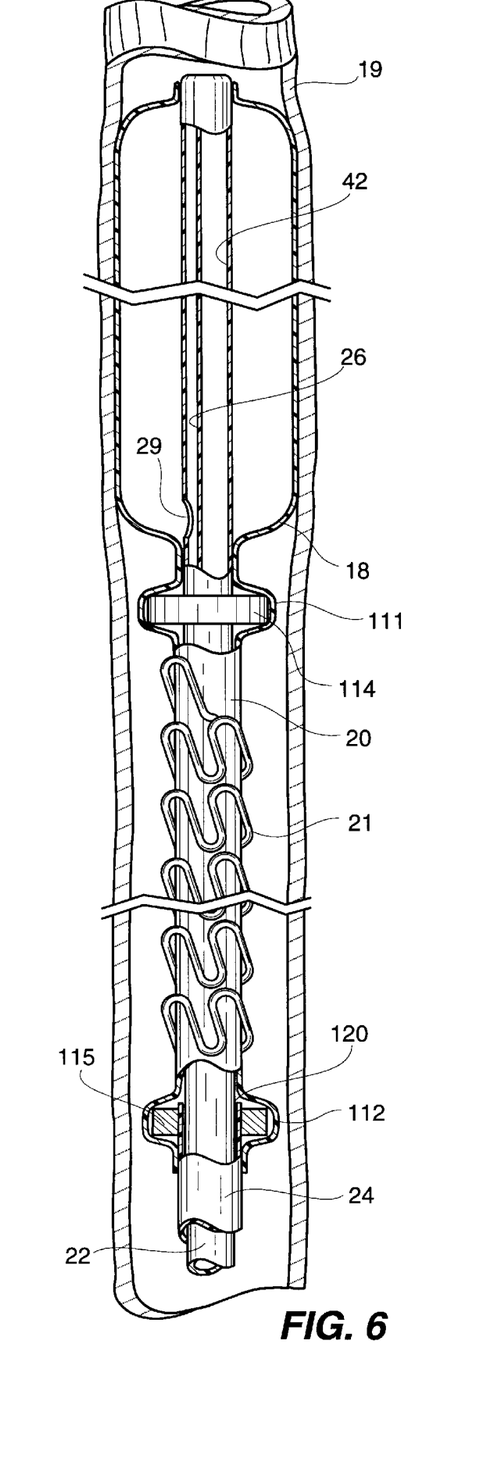
FIG. 6 is a longitudinal view, with portions broken away, of the distal end of the catheter shown in FIG. 1 after a more distal of two balloons has been inflated during a first step of the treatment for which the catheter assembly is to be used.

With the treatment, the catheter 10 is first introduced into the blood vessel section 19 to such a degree that the first balloon 18 is positioned at the stenosed section 19 which is to be dilated. Subsequently, a medium under pressure is supplied via the coupling 28 through the lumens 26 and 50 of the inner tube-like element 24. Via the opening 29 in the wall of the inner tube-like member 24, this medium under pressure flows into the balloon 18 as a result of which the balloon 18 expands. Consequently, the blood vessel section 19 will be dilated (FIG. 6).

Figure 7:
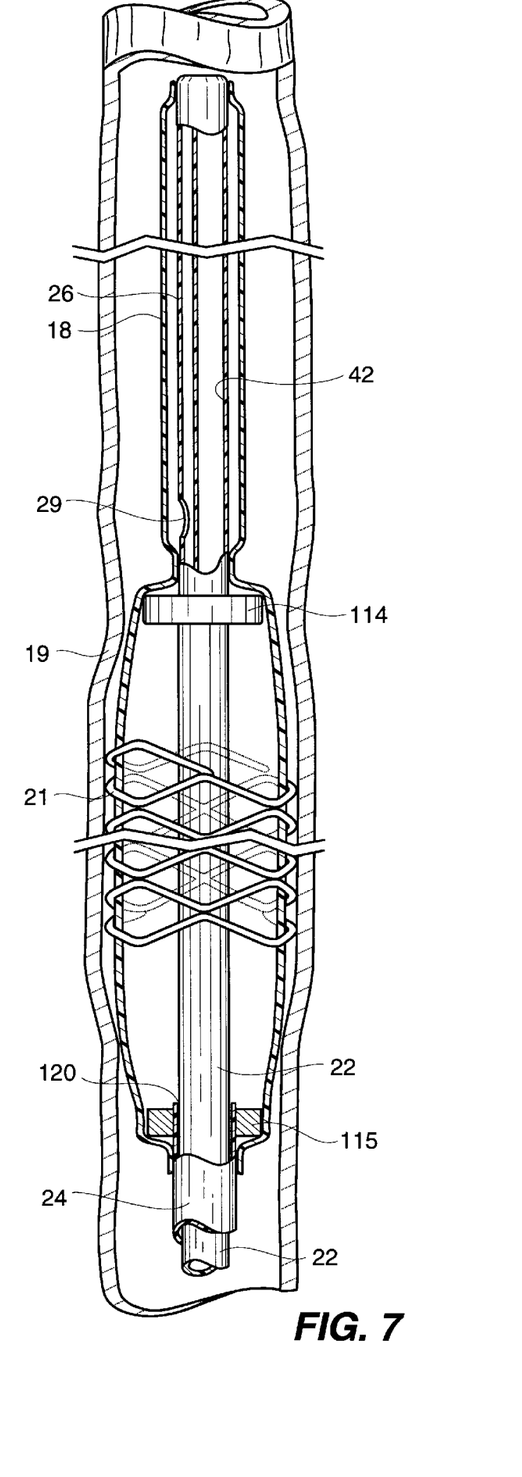
FIG. 7 is a longitudinal view, with portions broken away, of the distal end of the catheter shown in FIG. 1 after a more distal of two balloons has been deflated and a more proximal of the two balloons is inflated during a second step of the treatment for which the catheter assembly is to be used.

Next, the pressure inside the balloon 18 will be reduced, as a result of which it will resume its original shape, the catheter 10 is advanced further into the vessel so that the balloon 20 will be situated at the now dilated section 19 of the blood vessel. By supplying medium under pressure to the balloon 20 via coupling 32 and the annular interspace 30 between the tube-like elements 22 and 24, which annular interspace 30 is connected with the inside of the balloon 20 at the end of the outer tube-like element 22 as a ring-shaped opening 120, this balloon 20, and hence the stent 21, will be expanded. This situation has been illustrated in FIG. 7.

Figure 8:
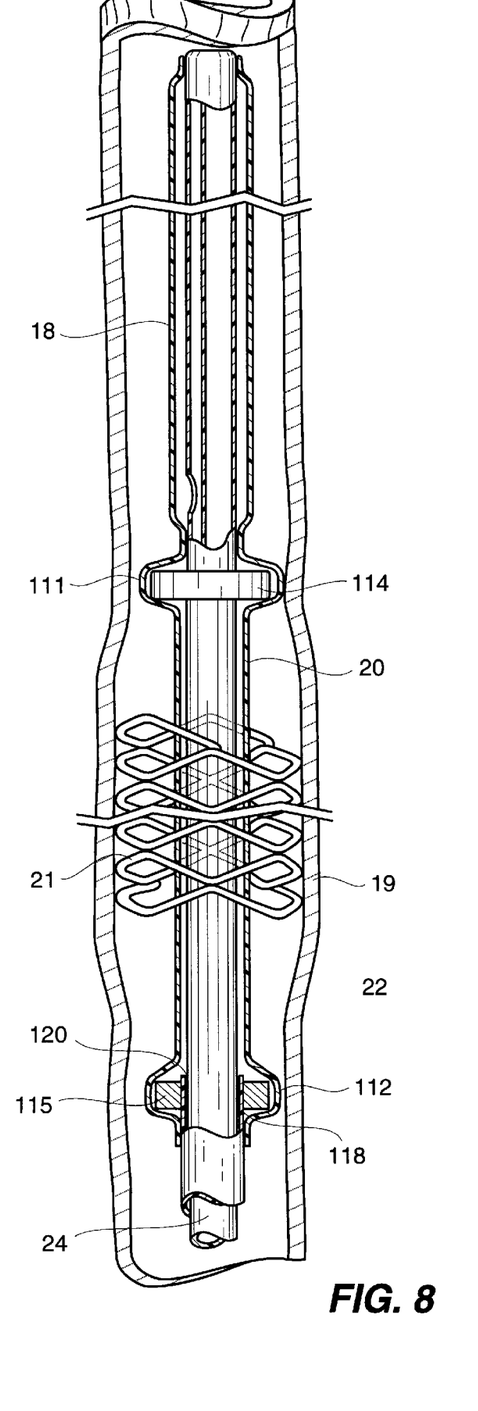
FIG. 8 is a longitudinal view, with portions broken away, of the distal end of the catheter shown in FIGS. 6 and 7 after both of the two balloons has been deflated to leave an expanded stent in place during a third step of the treatment for which the catheter assembly is to be used.
Figure 9:
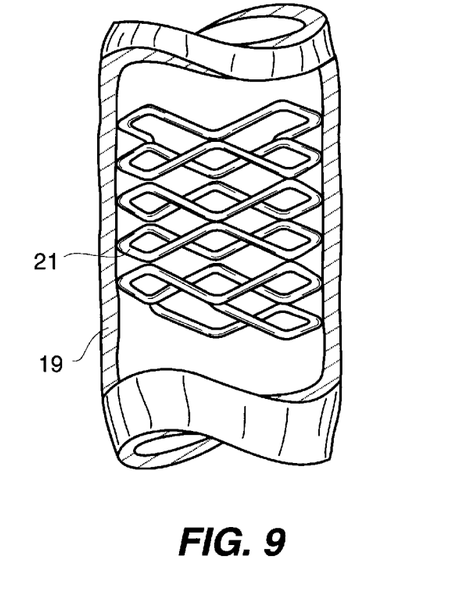
FIG. 9 is a longitudinal view, with portions broken away, of a treated blood vessel with the stent in position, following the removal of the catheter.

Subsequently, one allows the pressure in the balloon 20 to fall, as a result of which the balloon 20 will resume its original shape with small diameter as shown in FIG. 8. The catheter 10 can now be withdrawn, whereby as is shown in FIG. 9, the stent 21 remains behind in the blood vessel section 19, in order to support the wall thereof.

The balloons 18 and 20 possess different degrees of pliability. More in particular, the dilatation balloon 18 is more pliable than the balloon 20 used for expanding the stent 21.

During treatment, the catheter 10 is first advanced into the blood vessel section 19 that far, that the first balloon 18 is situated at the narrowed section 19 of the blood vessel to be dilated. Next a medium under pressure is supplied via the connecting member 28 and through the lumens 26 and 50 of the inner tube-like element 24. This medium under pressure flows via the opening 29 in the wall of the inner tube-like member 24 into the balloon 18, which will expand as a result.

Because of the relatively great pliability of the balloon 18, it will adapt well to the shape of the blood vessel section 19, so that the latter is subjected to a uniform load when being dilated.

Subsequently one allows the pressure inside the balloon 18 to drop, as a result of which it will regain its original shape. The catheter 10 is advanced further into the body, until the balloon 20 will be positioned in the dilated section 19 of the vessel. By now supplying medium under pressure to the balloon 20 via coupling 32 and the annular interspace 30 in between the tube-like elements 22 and 24, which annular interspace 30 is connected at the end 118 of the outer tube-like element 22 in the form of a ring-shaped opening 120 with the inside of the balloon 20, this balloon 20 and consequently the stent 21 will be expanded. This situation has been illustrated in FIG. 7.

As stated above, the balloon 20 is less pliable. The expansion is therefore less determined by possible resistance, so that a uniform expansion of the stent 21 is achieved.

Next one allows the pressure in the balloon 20 to drop again, as a consequence of which the balloon 20 regains its original shape with small diameter. The catheter 10 can now be withdrawn whereby the stent 21 remains behind in the blood vessel section 19 in order to support the wall thereof.

The catheter 10 and the accompanying stent shown in the figures only represent examples of embodiments. Other embodiments of a stent known as such, can be used in conjunction with the catheter 10. Because of the good axial fixation of the stent 21, the latter will remain positioned in a reliable manner at the site of the balloon 20 used for the purpose of expansion, so that it is not necessary to use a guiding catheter or a sheath.

The catheter 10 may comprise any number of balloon-shaped members, of which at least one comprises bulges on either side to retain a stent.

In the embodiment shown, the rings 114 and 115 have been made of material which is clearly visible when subjected to X-rays, so that the position of these rings 114, 115 and consequently the position of the stent 21, placed in between these bulges 111, 112, can be rendered clearly visible in a catherization laboratory.

The catheter assembly 8 is not limited to application with a catheter 10 for stent implantation. Other catheters with more balloon members, like for instance dilatation catheters comprising several dilatation balloons with different diameters, or dilatation catheters with occlusion balloon et cetera, can in a suitable manner be embodied in the catheter 10.

From the foregoing description it will be apparent that the catheter assembly 8 of the present invention has a number of advantages, some of which have been described above and others of which are inherent in the invention. For example, interference with the balloons 18 and 20 is avoided by the provision of a separate, short guidewire lumen 42 in a separate tube-like element 48 received in a lumen of the basic tubular body 24 and having a distal end mounted close to the distal end 16 of the tubular element through which it extends and a proximal end fixed within the wall hole 46.

Also, as noted above, modifications can be made to the catheter assembly 8 of the present invention without departing from the teachings of the invention. Accordingly, the scope of the invention is only to be limited as necessitated by the accompanying claims.

We claim:

1. A dual-balloon rapid-exchange stent delivery catheter system for introduction into a vessel of a body by a guidewire, comprising:

a tubular basic body having a proximal end, a distal end, a distal end section adjacent the distal end, and a central lumen;

a proximal hub affixed to the proximal end of the basic body;

a first and second relatively inelastic balloon arranged longitudinally adjacent each other and mounted on said distal end section of said basic body adjacent said distal end, wherein the first balloon is proximal from the second balloon;

a first and second inflation lumen extending along and within the basic body and communicating between a first and second inflation port formed in the proximal hub and the first and second balloon, respectively; such that the introduction of a pressurized fluid into the first and second inflation lumen will selectively inflate the first and second balloons, respectively;

a stent mounted on and crimped around the first balloon while the first balloon is in a deflated state, whereby the first balloon will expand and deploy the stent when inflated;

said basic body further having a wall and a wall hole in said wall located at a position between said distal end and said proximal end and being near to a proximal end of the most proximal first balloon, wherein the wall hole is also located nearer to the distal end of the basic body than the proximal end of the basic body;

a separate, guidewire receiving tubular member having a diameter less than the diameter of said tubular basic body and being received in said central lumen of said basic body, the guidewire receiving tubular member extending from a distal end opening at said distal end of said basic body to and just through said wall hole, and a proximal end of the guidewire receiving tubular member being fixed in said wall hole close to an outer edge of said wall hole but not extending beyond said wall of said basic body, the guidewire receiving tubular member adapted for slidingly receiving a guidewire in a rapid-exchange configuration.

2. The catheter of claim 1, further comprising an ultrasonic sensor.

3. The catheter of claim 1 wherein said proximal end of said guidewire receiving tubular member is beveled at a juncture of said guidewire receiving tubular member with said wall of said basic body so as to exhibit a smooth outer contour around said wall hole.

4. A dual-balloon rapid-exchange stent delivery catheter system for introduction into a vessel of a body by a guidewire, comprising:

a tubular basic body having a proximal end, a distal end, a distal end section adjacent the distal end, and a central lumen;

a proximal hub affixed to the proximal end of the basic body;

a first and second relatively inelastic balloon arranged longitudinally adjacent each other and mounted on said distal end section of said basic body adjacent said distal end, wherein the first balloon is proximal from the second balloon;

a first and second inflation lumen extending along and within the basic body and communicating between a first and second inflation port formed in the proximal hub and the first and second balloon, respectively; such that the introduction of a pressurized fluid into the first and second inflation lumen will selectively inflate the first and second balloons, respectively;

a stent mounted on and crimped around the first balloon while the first balloon is in a deflated state, whereby the first balloon will expand and deploy the stent when inflated;

said basic body further having a wall and a wall hole in said wall located at a position between said distal end and said proximal end and being near to a proximal end of the most proximal first balloon, wherein the wall hole is also located nearer to the distal end of the basic body than the proximal end of the basic body;

a separate, guidewire receiving tubular member having a diameter less than the diameter of said tubular basic body and being received in said central lumen of said basic body, the guidewire receiving tubular member extending from a distal end opening at said distal end of said basic body to and just through said wall hole, and a proximal end of the guidewire receiving tubular member being fixed in said wall hole close to an outer edge of said wall hole but not extending beyond said wall of said basic body, the guidewire receiving tubular member adapted for slidingly receiving a guidewire in a rapid-exchange configuration, said wall hole being formed by a section of said wall of said basic body, just proximal of the first balloon, is folded radially inwards in said basic body close to said wall hole, and the proximal end of the guidewire receiving tubular member being fixed on the inwardly folded wall section.

* * * * *